(12) United States Patent
Fercher

(10) Patent No.: US 6,922,250 B2
(45) Date of Patent: Jul. 26, 2005

(54) OPTICAL MULTIPLEX SHORT COHERENCE INTERFEROMETRY ON THE EYE

(75) Inventor: Adolf Friedrich Fercher, Vienna (AT)

(73) Assignee: Carl Zeiss Meditec AG, Jena (DE)

( * ) Notice: Subject to any disclaimer, the term of this patent is extended or adjusted under 35 U.S.C. 154(b) by 256 days.

(21) Appl. No.: 10/229,464

(22) Filed: Aug. 28, 2002

(65) Prior Publication Data
US 2003/0072007 A1 Apr. 17, 2003

(30) Foreign Application Priority Data
Aug. 28, 2001 (DE) .......................... 101 42 001

(51) Int. Cl.⁷ .............................. G01B 9/02
(52) U.S. Cl. .................................. 356/497
(58) Field of Search ................ 356/497, 479, 356/503, 504, 511, 450

(56) References Cited
U.S. PATENT DOCUMENTS
6,480,285 B1 * 11/2002 Hill ........................... 356/492

OTHER PUBLICATIONS

E. Moreno–Barriuso, R. Navarro, *J. Opt. Soc. Am. A*, vol. 17 (2000): 974–985.
A. F. Fercher and C. K. Hitzenberger, *Springer Series in Optical Sciences* (ed. T. Asakura), vol. 4, Springer Verlag, Berlin 1999.

* cited by examiner

*Primary Examiner*—Andrew H. Lee
(74) *Attorney, Agent, or Firm*—Reed Smith LLP

(57) ABSTRACT

The invention is directed to the detection and imaging of the internal geometry of the eye, particularly of the important components for imaging in the eye such as the cornea, lens, vitreous body and retinal surface, by multichannel short coherence interferometry. A method and arrangement for obtaining topograms and tomograms of the eye structure by many simultaneously recorded interferometric depth scans through transversely adjacent points in the pupil using spatially coherent or spatially partially coherent light sources. The depth scan is carried out by changing the optical length of the interferometer measurement arm by means of a retroreflector. By continuously displacing the retroreflector, the z-position of the light-reemitting point in the eye can be determined by means of the occurring interference. It is possible to record depth scans simultaneously through the use of spatially coherent or spatially partially coherent light beams comprising a plurality of partial beams.

6 Claims, 4 Drawing Sheets

OPTICAL MULTIPLEX SHORT COHERENCE INTERFEROMETRY ON THE EYE

CROSS-REFERENCE TO RELATED APPLICATIONS

This application claims priority of German Application No. 101 42 001.3, filed Aug. 28, 2001, the complete disclosure of which is hereby incorporated by reference.

BACKGROUND OF THE INVENTION a) Field of the Invention

The present invention is directed to the detection and imaging of the internal geometry of the eye, particularly of the important components for imaging in the eye such as the cornea, lens, vitreous body and retinal surface, by means of multiplex multichannel short coherence interferometry.

b) Description of the Related Art

Owing to new developments in ophthalmology characterized by many different types of operative procedures on the eye lens (e.g., cataract surgery) and on the cornea (refractive cornea surgery), there is a considerable demand for measurement methods which show the optically active geometry of the eye quantitatively. One task in this connection is the measurement of the imaging quality of the eye. Various methods for detecting the imaging quality of the eye are already known: subjective methods requiring the cooperation of the test subject and objective methods which dispense with the cooperation of the test subject in the measurement in the stricter sense. Subjective methods are rarely used due to the required cooperation of the test subject for rigorous clarification of clinical questions. Also, the previously known objective methods for detecting aberrations in the eye allow only limited access to the geometric structure of the eye because they only show the total effect of all optically active structures of the eye and can not clearly separate the influences of individual components. A recent overview of these questions and a comparison of two modem subjective methods for measuring the aberrations of the eye are found, for example, in E. Moreno-Barriuso, R. Navarro, *J. Opt. Soc. Am. A*, Vol. 17 (2000): 974–985.

Short coherence interferometry offers an objective method for the quantitative detection of the optically active geometry of the eye. In this method, interferometric measurement beams of a two-beam interferometer are directed to the object and penetrate into the depth of the latter. The depth positions of light-reemitting locations are measured along these measurement light beams approximately in the direction of the visual axis or optic axis of the eye. When measuring by means of these depth scans, as they are called, the length of the reference beam is continuously changed, e.g., by axial displacement of the reference mirror, and the short coherence interferogram is accordingly registered along the depth coordinate of the measurement beam in the measurement object. When the length of the reference beam within the coherence length, that is, within the so-called coherence window, matches the length of the measurement beam to a light-reemitting structure, interference occurs at the interferometer output. This interference generates an electric AC signal at the photoelectric detector at the interferometer output, which AC signal represents the light-reemitting structure. The instantaneous length of the reference beam gives the associated depth position of this light-reemitting location in the measurement beam. In order to ensure a meaningful transverse resolution, the measurement beam is focused on the object structure under consideration or a dynamic focus is used which scans the object depth in longitudinal direction synchronously with the coherence window. The electric signal of the photoelectric detector at the interferometer output then contains the depth structure along the measurement beam. The topography of the intraocular structures can then be determined from depth scans of the kind mentioned above which are carried out through transversely adjacent pupil points of the eye; tomographic images can also be synthesized from an appropriate quantity of these transversely adjacent depth scans. These methods are known as optical coherence tomography and optical coherence topography and are described in A. F. Fercher and C. K. Hitzenberger, *Springer Series in Optical Sciences* (ed. T. Asakura), Vol. 4, Springer Verlag, Berlin 1999.

The described short coherence interferometry has the disadvantage that many individual transversely adjacent depth scans must be carried out along individual measurement beams one after the other in a time-consuming manner to obtain topograms or tomograms. In particular, the use of a method of this type on patients is problematic.

OBJECT AND SUMMARY OF THE INVENTION

Therefore, it is the primary object of the invention to indicate methods and arrangements for obtaining topograms and tomograms of the eye structure by means of many simultaneously recorded multiplex short coherence interferometric depth scans through transversely adjacent points in the pupil.

This object is met in that the short coherence interferometric depth scan is carried out on the eye by means of a transversely expanded primary measurement image of spatially coherent or spatially partially coherent light sources in the measurement arm of the interferometer, a primary reference image of the spatially coherent or spatially partially coherent light source is generated in the reference arm of the interferometer, and both primary images are imaged at the interferometer output in secondary, coincident images on one-dimensional or two-dimensional photo detector arrays for detecting the simultaneously occurring photoelectric depth scan signals from transversely adjacent pupil points.

Another object is to achieve a dynamic focusing so that the measurement image scans the object depth synchronously with the coherence window.

This object is met in that the short coherence interferometric depth scan is carried out by changing the optical length of the interferometer measurement arm and the interferometer light source is imaged in the primary measurement image in the eye via an intermediate image by means of optics whose focal length corresponds approximately to the optical length of the schematic eye.

DESCRIPTION OF THE PREFERRED EMBODIMENTS

By "short coherence" is meant that light of short coherence length is used in this interferometry method. In this connection, the optical path length of the measurement beam of a two-beam interferometer is scanned by matching or tuning the length of the reference beam after interference occurs. During this depth scan, as it is called, the reference mirror is moved along the axis of the reference beam. When the path length of the reference beam from the beam splitter to the measurement location and back within the coherence length is equal to the path length of the measurement beam from the beam splitter to a light-reemitting point in the object (eye) and back to the beam splitter, interference occurs at the interferometer output. The area at the measurement location contributing to this interference is called the "coherence window". By continuously displacing the reference mirror, the z-position of light-reemitting points in the object is recorded by means of the interference occurring at a photodetector at the interferometer output. The determination of the z-position is carried out with an accuracy given approximately by the coherence length $$l_c \cong \frac{\lambda^2}{\Delta\lambda}$$

of the light which is used; in this case, $\lambda$ is the mean wavelength and $\Delta\lambda$ is the wavelength bandwidth of the radiation that is used. Accordingly, the coherence window of a depth scan has an approximate length $l_c$. At the present time, exclusively spatially coherent light sources are used to carry out the depth scan.

Spatially coherent light sources are lasers and superluminescent diodes in transverse monomode operation, whereas spatially partially coherent light sources are incandescent lamps, halogen lamps, plasma low-pressure lamps and plasma high-pressure lamps, but also superluminescent diodes in transverse multimode operation as well as all lasers in transverse multimode operation.

Figure 1:
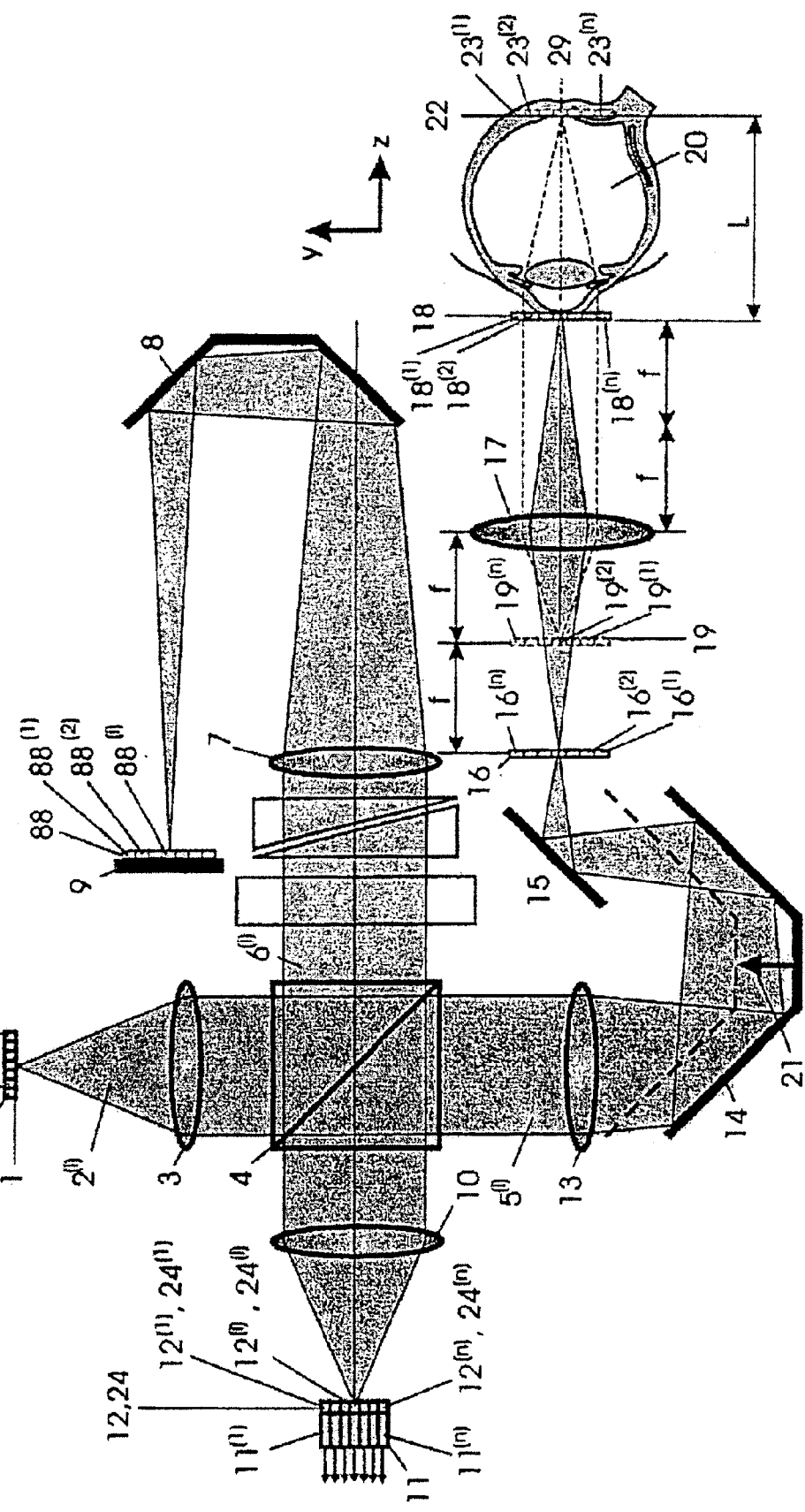
FIG. 1 illustrates a one-dimensional version of the multiplex short coherence interferometry method, according to the invention, for measuring the internal geometry of the eye by means of a transversely expanded and spatially partially coherent light source 1.

FIG. 1 shows the beam path of the ophthalmologic short coherence interferometer with an expanded spatially partially coherent light source 1. This light source comprises the spatially partially coherent partial light sources $1^{(1)}$, $1^{(2)}$, ..., $1^{(n)}$. A partial beam exiting from the partial light source $1^{(i)}$ of the expanded spatially partially coherent light source 1 is designated by $2^{(i)}$ (where $1 \leq i \leq n$). This partial beam is collimated by optics 3 and split by beam splitter 4 into measurement beam $5^{(i)}$ and reference beam $6^{(i)}$. The reference beam $6^{(1)}$ is reflected by optics 7 via the retroreflector 8 to the reference mirror 9 and is focused at the latter in the partial image $88^{(i)}$ of the spatially partially coherent partial light source $1^{(i)}$. The light of the reference beam $6^{(i)}$ reflected by the reference mirror 9 is directed via the retroreflector 8, optics 7, beam splitter 4 and optics 10 to the photodetector array 11 with n photodetectors at the interferometer output and is focused there in the partial image $12^{(i)}$ of the secondary reference image 12 of the partial light source $1^{(i)}$. The same thing happens in an analogous manner with all of the partial beams $2^{(1)}, 2^{(2)}, \ldots, 2^{(n)}$ which exit from the rest of the partial light sources $1^{(1)}, 1^{(2)}, \ldots, 1^{(n)}$, although they are not shown in FIG. 1. However, it is evident that these light bundles generate the partial images $88^{(1)}$, $88^{(2)}, \ldots, 88^{(n)}$ on the reference mirror 9 and the partial images $12^{(1)}, 12^{(2)}, \ldots, 12^{(n)}$ of the secondary reference image 12 on the photodetector 11 at the interferometer output.

The partial beams $5^{(1)}, 5^{(2)}, \ldots, 5^{(n)}$ which penetrate the beam splitter 4 form the measurement beam bundle. This measurement beam bundle is focused by the optics 13 via the retroreflector 14 and the deflecting mirror 15 in the intermediate image 16 with partial images $16^{(1)}, 16^{(2)}, \ldots, 16^{(n)}$. The intermediate image 16 is located two focal lengths f of the optics 17 in front of the latter. Therefore, the intermediate image 16 is imaged in an imaging scale of 1:1 by optics 17 in the primary measurement image 18 with partial images $18^{(1)}, 18^{(2)}, \ldots, 18^{(n)}$ in a plane at the cornea of the eye 20 normal to the optic axis 29.

When the retroreflector 14 moves in the direction of the beam splitter 4 by distance $\Delta z$, as is indicated in FIG. 1 by the arrow 21, the optical length of the measurement beam path is reduced by $2\Delta z$. The partial images $16^{(1)}, 16^{(2)}, \ldots, 16^{(n)}$ of the light source 1 are accordingly displaced into the positions $19^{(1)}, 19^{(2)}, \ldots, 19^{(n)}$ shown by dashes: when $\Delta z=f/2$, that is, when $\Delta z$ is equal to half the focal length of optics 17, the partial images $16^{(1)}, 16^{(2)}, \ldots, 16^{(n)}$ of the intermediate image of the light source 1 are now located in the front focal plane of optics 17 and the primary measurement image 18 with partial images $18^{(1)}, 18^{(2)}, \ldots, 18^{(n)}$ is imaged by the optics of the eye 20 on the fundus 22 in the positions $23^{(1)}, 23^{(2)}, \ldots, 23^{(n)}$ indicated by dashes. For displacements of the retroreflector 14 by distances less than $\Delta z=f/2$, the primary measurement image 18 is imaged in positions between the cornea and fundus with partial images $18^{(1)}, 18^{(2)}, \ldots, 18^{(n)}$.

By displacing the retroreflector 14 by distance $\Delta z=f/2$, the eye is scanned by the primary measurement image 18 of the light source 1 with partial images $18^{(1)}, 18^{(2)}, \ldots, 18^{(n)}$ from the cornea to the fundus.

For short coherence interferometric measurement, it is also necessary for the coherence window to be located at the respective location of the primary measurement image 18. For this purpose, the focal length f of optics 17 is selected, according to the invention, so as to equal the optical length of the eye from the cornea to the fundus. The optical length of the eye is its geometric length L multiplied by the average group index of the eye $n_G$. Gullstrand states that the average group index $n_G$ of the schematic human eye, for example, for light with an average wavelength of $\lambda=780$ nm, has the value $n_G=1.3549$.

When the partial images $18^{(1)}, 18^{(2)}, \ldots, 18^{(n)}$ of the primary measurement image 18 strike light-reemitting points in the eye, the re-emitted light rays are imaged on the photodetector 11 via the optics of the eye, optics 17, deflecting mirror 15, retroreflector 14, optics 13, beam splitter 4 and optics 10, and form partial images $24^{(1)}, 24^{(2)}, \ldots, 24^{(n)}$ of the secondary measurement image 24 on the photodetector 11. When the partial images $24^{(1)}, 24^{(2)}, \ldots, 24^{(n)}$ completely cover the partial images $12^{(1)}, 12^{(2)}, \ldots, 24^{(n)}$ which is possible by means of appropriate adjustment of the interferometer beam splitter 4, interference occurs at these locations and can be detected simultaneously by the detector array. There are n short coherence interferometric reference beams corresponding to partial images $12^{(i)}$, (i=1 ... n) and n short coherence interferometric measurement beams corresponding to partial images $24^{(i)}$, (i=1 ... n). Accordingly, it is possible to carry out a large number of depth scans through the eye in a parallel and simultaneous manner.

Figure 2:
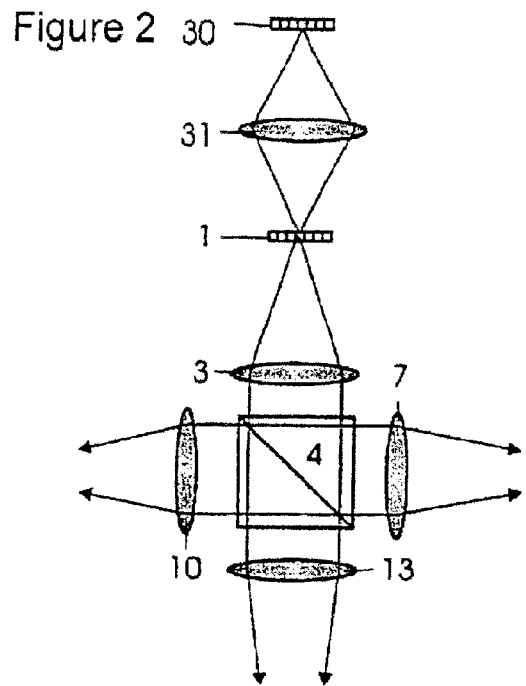
FIG. 2 illustrates a one-dimensional version of the multiplex short coherence interferometry method, according to the invention, for measuring the internal geometry of the eye by means of a transversely expanded light source, the interferometer light source 1 being formed by imaging an actual or concrete light source 30.
Figure 3:
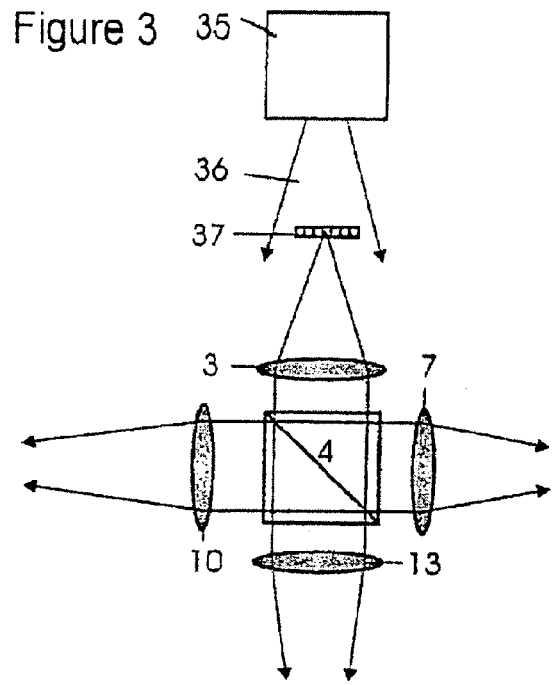
FIG. 3 illustrates a one-dimensional version of the multiplex short coherence interferometry method, according to the invention, for measuring the internal geometry of the eye by means of a transversely expanded light source 1, wherein a cross section from a light bundle 36 is used as interferometer light source 37.

Obviously, instead of the light source 1, an image of a light source can also be used. An example is shown in FIG. 2. A light source, designated by 30, is imaged by optics 31 at the location of the interferometric light source 1 at the interferometer input of the interferometer shown in FIG. 1. Instead of a concrete light source, any cutout or section from a light bundle can also be used as a light source. An example is shown in FIG. 3. In this case, an optional light source is designated by 35 and the light bundle proceeding from it is designated by 36. In this case, the section from the light bundle 36 at location 37 at the interferometer input serves as an interferometer light source for the interferometer.

It should also be noted that a Doppler displacement of the measurement light is carried out by moving the retroreflector 14, so that an electric AC signal which enables bandpass filtering for reducing noise is formed at the individual photodetectors $11^{(1)}, 11^{(2)}, \ldots, 11^{(n)}$.

The use of spatially partially coherent light sources 1 reduces the crosstalk of the partial beams because scattered light from one partial beam is not fully capable of interference with scattered light from another partial beam. Nevertheless, it may also be useful to realize this method with spatially coherent light sources, for example, because a wide variety of these light sources is commercially obtainable. A corresponding arrangement is shown in FIG. 4.

Figure 4:
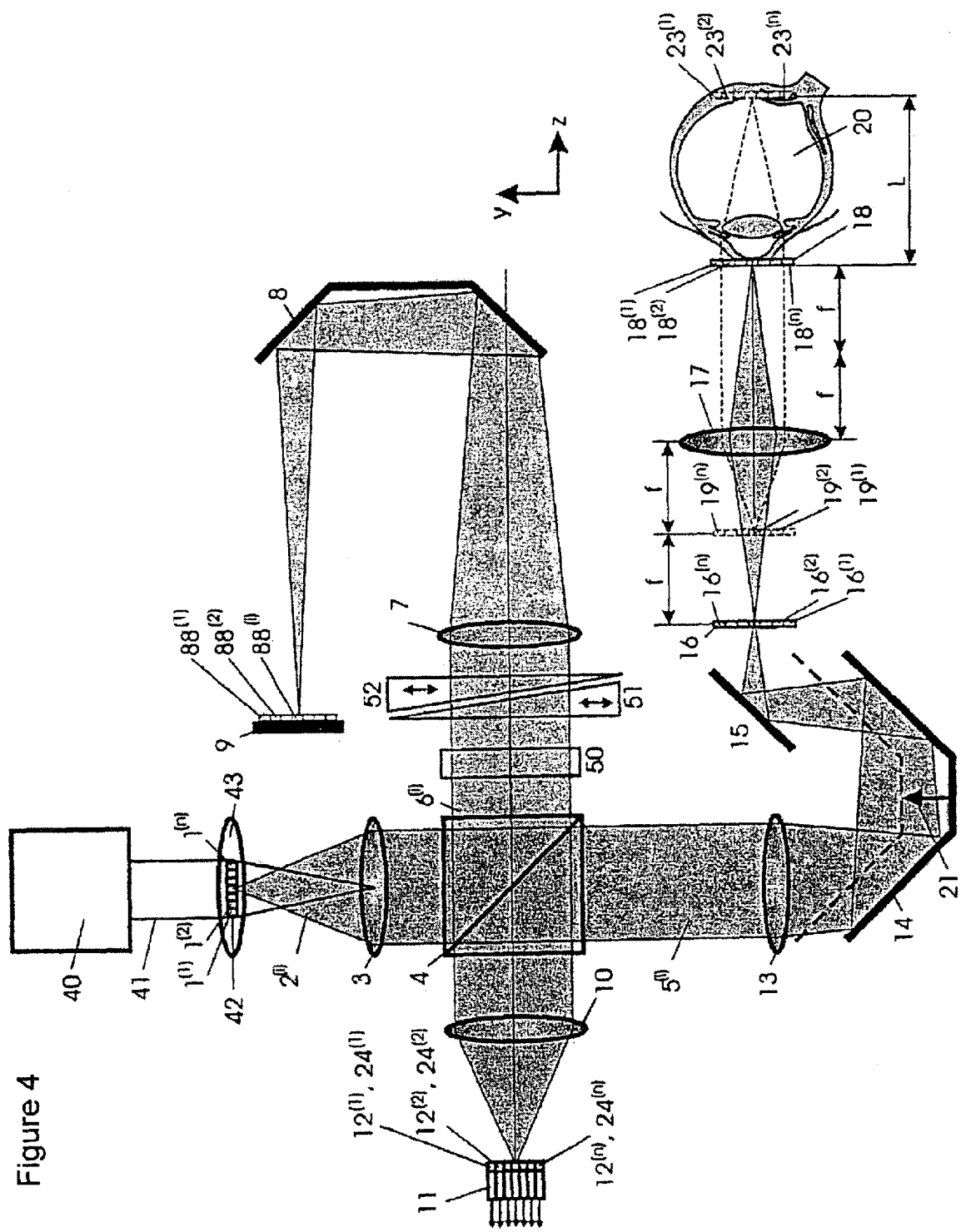
FIG. 4 illustrates a one-dimensional version of the multiplex short coherence interferometry method, according to the invention, for measuring the internal geometry of the eye by means of a transversely expanded spatially coherent light source 42, wherein a superluminescent diode operating in transverse fundamental mode or a multimode laser operating in transverse fundamental mode is used as a light source 40.

In FIG. 4, a spatially coherent and temporally short coherent light source, e.g., a superluminescent diode in transverse fundamental mode operation or a multimode laser in transverse fundamental mode operation, is designated by 40. The optics 43 focus the light bundle 41 in the entrance pupil of the interferometer. An optional beam cross section 42 in the beam 41 emitted by this light source serves as an interferometer light source for the short coherence interferometer. As in the short coherence interferometer according to FIG. 1, the spatially coherent partial light sources $42^{(1)}, 42^{(2)}, \ldots, 42^{(n)}$ are imaged in the reference arm in the primary reference images $88^{(1)}, 88^{(2)}, \ldots, 88^{(n)}$ on the one hand and in the measurement arm in the primary measurement images $18^{(1)}, 19^{(2)}, \ldots, 18^{(n)}$ on the other hand and, further, in coincident manner on the photodetector array 11 in partial images $12^{(1)}, 12^{(2)}, \ldots, 12^{(n)}$ and $24^{(1)}, 24^{(2)}, \ldots, 24^{(n)}$. In other respects, the beam path can be identical to the interferometer according to FIG. 1.

In short coherence interferometry, broadband light is used. When one of the interferometer beams passes through dispersive media, the coherence length is increased, which worsens the depth resolution of the short coherence interferometry. This can be compensated by carefully balancing the dispersion in both interferometer arms. For this purpose, the dispersion must be the same in both interferometer arms. This means, for one, that the glass paths of the two interferometer beams must be of equal length. Since the length of the measurement distance varies along the depth of the eye, a varying amount of dispersion must also be achieved in the reference arm. According to the invention, this can be achieved approximately in such a way that a glass path corresponding to the dispersion of half of the length of the eye is installed in a fixed manner in the reference arm. When a plane plate 50 of BK7 is used for this purpose, its thickness must be approximately 6.3 mm with a wavelength of $\lambda=800$ nm for the schematic eye, for example. The dispersion of the eye can also be compensated dynamically during the depth scan. Two prisms 51 and 52 with prism angle a which are arranged one behind the other in the reference beam are suitable for this purpose. Different glass paths and corresponding dispersions can be adjusted by displacement transverse to the beam axis as indicated by the double arrows in the drawing. By suitable selection of the prism angle a, a dispersion corresponding to the respective position of the coherence window in the eye can be adjusted dynamically by displacing the prisms 51 and 52 synchronous to the retroreflector 14.

Figure 6:
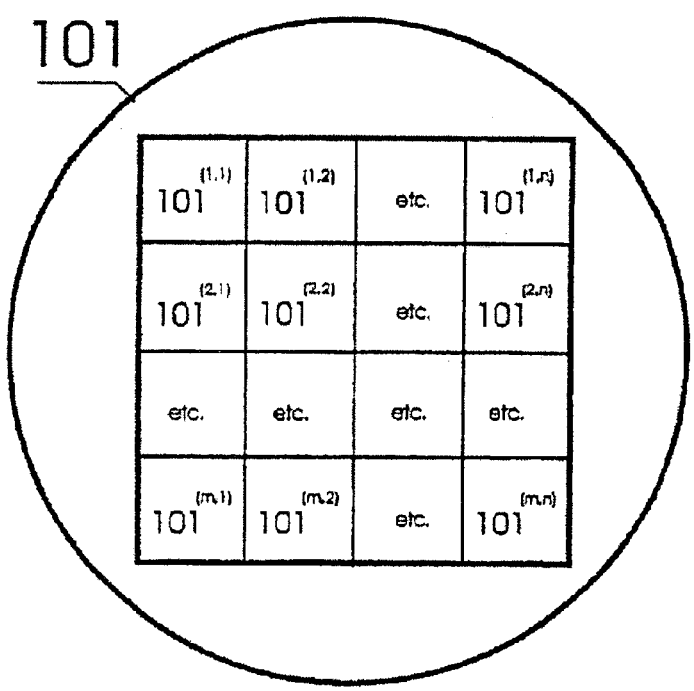
FIG. 6 defines the designation of the partial light sources in two-dimensional optical multiplex short coherence interferometry.
Figure 5:
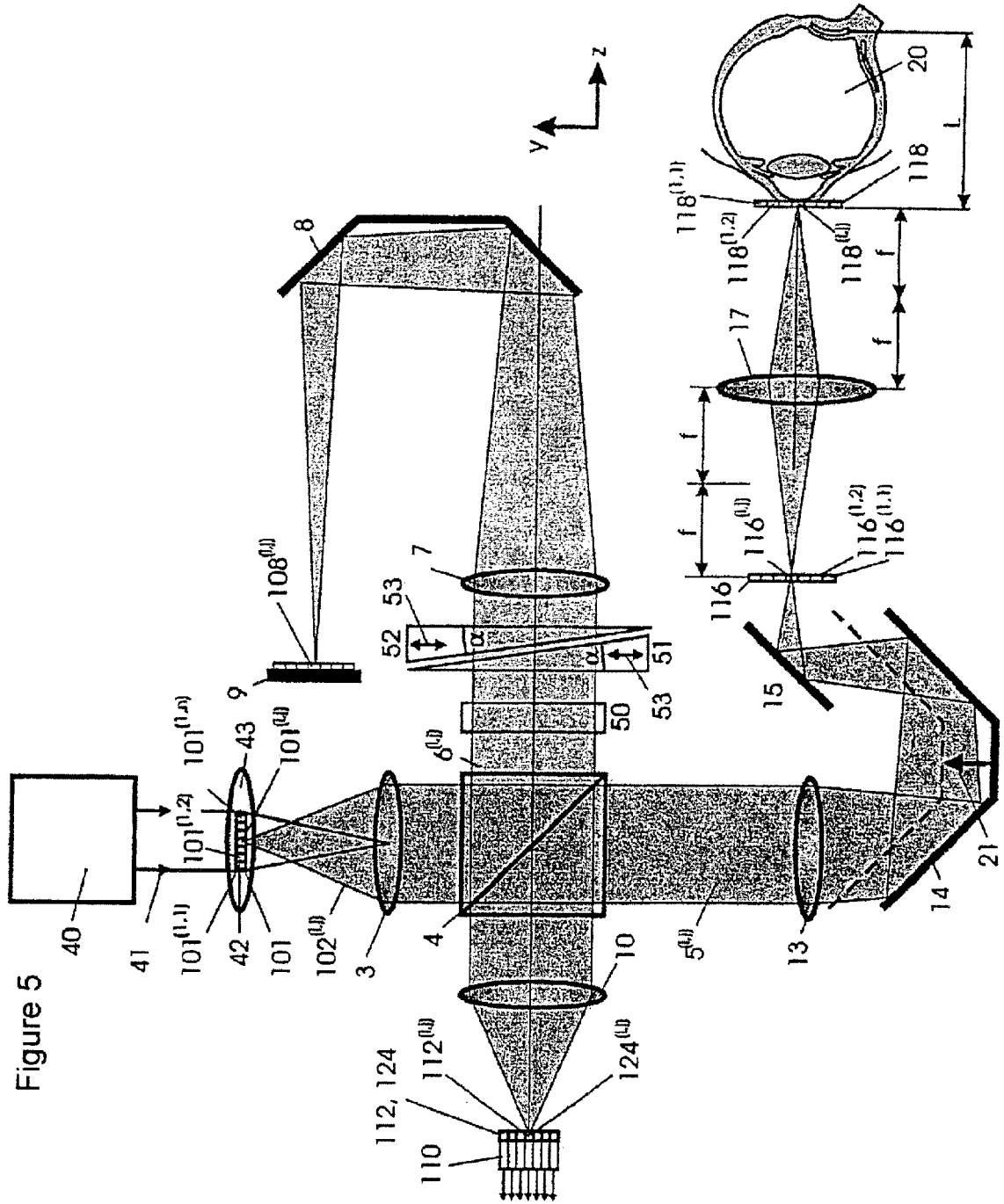
FIG. 5 illustrates a two-dimensional version of optical multiplex short coherence interferometry.

The method which has been described using the example of a one-dimensional detector array 11 can be applied to two-dimensional parallel optical multiplex short coherence interferometry through the use of a two-dimensional detector array 110. This is shown in FIG. 5. In this case, the section from light bundle 41 at any position 42 serves as interferometer light source 101. A spatially coherent or spatially partially coherent light source is designated by 40. A concrete spatially coherent or spatially partially coherent light source can also be used as interferometer light source 101. In either case, a flat two-dimensional region is used by the interferometer light source 101 as is indicated in FIG. 6. This light source area comprises partial light sources $101^{(1,1)}, 101^{(1,2)}, \ldots, 101^{(1,n)}; 101^{(2,1)}, 101^{(2,2)}, \ldots, 101^{(2,n)}$, etc. to $101^{(m,n)}$. The numbers m and n are equal to the column and row numbers of the photodetector array 110. Depending on the photodetector array, m and n can be large numbers, for example, 20 or 1024. A partial beam exiting from the partial light source $101^{(i,j)}$ of the interferometer light source 101 is designated by $102^{(i,j)}$. This partial beam is collimated by optics 3 and split by the beam splitter 4 into measurement beam $5^{(i,j)}$ and reference beam $6^{(i,j)}$. The reference beam $6^{(i,j)}$ is reflected by the optics 7 to the reference mirror 9 by the retroreflector 8 and is focused at the reference mirror 9 in the primary reference partial image $108^{(i,j)}$ of the partial light source $101^{(i,j)}$. The light of the reference beam $6^{(i,j)}$ reflected by the reference mirror 9 is directed in the secondary reference partial image 112 on the photodetector array 110 with m×n photodetectors at the interferometer output by retroreflector 8, optics 7, beam splitter 4 and optics 10 and forms the secondary reference image $112^{(i,j)}$ of the partial light source $101^{(i,j)}$. The same thing happens in an analogous manner with all of the partial beams $102^{(1,1)}, 102^{(1,2)}, \ldots$, etc., not shown in FIG. 5, which exit from the rest of the partial light sources $101^{(1,1)}, 101^{(1,2)}, \ldots$, etc. These light bundles also generate primary partial reference images $108^{(1,1)}, 108^{(1,2)}, \ldots$, etc. on the reference mirror 9 and secondary partial reference images $112^{(1,1)}, 112^{(1,2)}, \ldots$, etc. on the photodetector 110 at the interferometer output.

The partial beams $5^{(1,1)}, 5^{(1,2)}, \ldots$, etc. which penetrate the beam splitter 4 form the measurement beam bundle. The latter is focused by optics 13 via the retroreflector 14 and the deflecting mirror 15 in the intermediate image 116 with partial images $116^{(1,1)}, 116^{(1,2)}, \ldots,$. The intermediate image 116 is located two focal lengths f of optics 17 in front of the latter. Therefore, the intermediate image 116 is imaged in an imaging scale of 1:1 by optics 17 in the primary measurement image 118 with partial images $118^{(1,1)}, 118^{(1,2)}, \ldots, 118^{(m,n)}$ in a plane at the cornea of the eye 20 normal to the optic axis.

Here, also, by displacing the retroreflector 14 by distance $\Delta z=f/2$, the eye is scanned by the primary measurement image 118 with partial images $118^{(1,2)}, 118^{(1,2)}, \ldots, 118^{(m,n)}$ from the cornea to the fundus. Again, the focal length f of the optics 17 is selected, according to the invention, so as to be equal to the optical length of the eye from the cornea to the fundus. When the partial images $118^{(1,1)}, 118^{(1,2)}, \ldots, 118^{(m,n)}$ of the primary measurement image 118 strike light-reemitting points on the eye, the re-emitted light rays are imaged on the photodetector 110 via the optics of the eye, optics 17, deflecting mirror 15, retroreflector 14, optics 13, beam splitter 4 and optics 10 and form secondary partial images $124^{(1,1)}, 124^{(1,2)}, \ldots, 124^{(m,n)}$ on the photodetector 110. When the secondary partial images $124^{(1,1)}, 124^{(1,2)}, \ldots, 124^{(m,n)}$ of the measurement beam completely cover the partial images $112^{(1,1)}, 112^{(1,2)}, \ldots, 112^{(m,n)}$ of the reference beam, interference occurs at these locations, all of which can be read out simultaneously by the detector array 110. There are m×n short coherence interferometric reference beams corresponding to partial images $112^{(i,j)}$, (i=1 ... m; j=1 ... n) and m×n short coherence interferometric measurement beams corresponding to partial images $124^{(i,j)}$, (i=1 ... m; j=1 ... n). Accordingly, it is possible to carry out m × n depth scans through the eye simultaneously in multiplex mode.

As in the one-dimensional example, the dispersion of the eye can be realized either approximately by means of a fixed glass path in the reference arm, for example, by means of a plane plate 50, or can be compensated statically or dynamically by means of two prisms 51 and 52 which are arranged one behind the other in the reference beam and which can be displaced transverse to the beam axis in direction of the double arrow 53 during the depth scan.

While the foregoing description and drawings represent the present invention, it will be obvious to those skilled in the art that various changes may be made therein without departing from the true spirit and scope of the present invention.

What is claimed is:

1. A method for obtaining topograms and tomograms of the eye structure by many simultaneously recorded short coherence interferometric depth scans through transversely adjacent points in the pupil, comprising the steps of:

providing an interferometer having a measurement arm, a reference arm, a reference beam and an output;

carrying out a short coherence interferometric depth scan on the eye by a transversely expanded primary measurement image of spatially coherent or spatially partially coherent light sources in the measurement arm of the interferometer;

generating a primary reference image of the spatially coherent or spatially partially coherent light source in the reference arm of the interferometer;

imaging both primary images at the interferometer output in secondary, coincident images on one-dimensional or two-dimensional photo detector arrays for detecting the simultaneously occurring photoelectric depth scan signals from transversely adjacent pupil points; and dynamically focusing of the measurement image synchronous with the coherence window, wherein the short coherence interferometric depth scan is carried out by changing the optical length of the interferometer measurement arm by a retroreflector and the primary measurement image is formed in the eye by imaging the interferometer light source via an intermediate image by optics whose focal length corresponds approximately to the optical length of the schematic eye.

2. The method according to claim 1, wherein dispersion of the eye is compensated by a plane plate in the reference beam.

3. The method according to claim 1, wherein dispersion of the eye is compensated by two prisms which are moved in the reference beam synchronous to the retroreflector.

4. An arrangement for obtaining topograms and tomograms of the eye structure by many simultaneously recorded short coherence interferometric depth scans through transversely adjacent points in the pupil comprising:

an interferometer having a measurement arm, a reference arm, a reference beam and an output;

means for carrying out a short coherence interferometeric depth scan on the eye by a transversely expanded primary measurement image of spatially coherent or partially coherent light sources in the measurement arm of the interferometer;

means for generating a primary reference image of the spatially coherent or spatially partially coherent light source in the reference arm of the interferometer;

means for imaging both primary images at the interferometer output in secondary, coincident images on one-dimensional or two-dimensional photo detector arrays for detecting simultaneously occurring photoelectric depth scan signals from transversely adjacent pupil points; and means for dynamically focusing a measurement image synchronous with a coherence window wherein the interferometer measurement arm has an optical length and the short coherence interferometric depth scan is carried out by changing the optical length of the interferometer measurement arm by a retroflector light source via an intermediate image by optics whose focal length corresponds approximately to the optical length of the schematic eye.

5. The arrangement according to claim 4, wherein dispersion of the eye is compensated by a plane plate in the reference beam.

6. The arrangement according to claim 4, wherein dispersion of the eye is compensated by two prisms which are moved in the reference beam synchronous to the retroreflector.

* * * * *